United States Patent
Rao et al.

(10) Patent No.: US 8,163,964 B2
(45) Date of Patent: Apr. 24, 2012

(54) PROCESSES FOR PRODUCING PENTAFLUOROPROPENES AND CERTAIN AZEOTROPES COMPRISING HF AND CERTAIN HALOPROPENES OF THE FORMULA $C_3HClF_4$

(75) Inventors: Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 347 days.

(21) Appl. No.: 12/514,348

(22) PCT Filed: Nov. 15, 2007

(86) PCT No.: PCT/US2007/024065
§ 371 (c)(1),
(2), (4) Date: May 11, 2009

(87) PCT Pub. No.: WO2008/060616
PCT Pub. Date: May 22, 2008

(65) Prior Publication Data
US 2010/0051853 A1 Mar. 4, 2010

Related U.S. Application Data

(60) Provisional application No. 60/859,173, filed on Nov. 15, 2006.

(51) Int. Cl.
*C07C 17/00* (2006.01)
(52) U.S. Cl. ...................................... 570/156; 570/155
(58) Field of Classification Search .................. 570/155, 570/156
See application file for complete search history.

(56) References Cited

U.S. PATENT DOCUMENTS

| | | | | |
|---|---|---|---|---|
| 3,381,042 A | * | 4/1968 | Yale | ............................... 570/172 |
| 5,396,000 A | | 3/1995 | Nappa et al. | |
| 6,369,284 B1 | | 4/2002 | Nappa et al. | |
| 6,958,424 B1 | | 10/2005 | Nair et al. | |
| 7,687,670 B2 | * | 3/2010 | Nappa | ........................... 570/156 |
| 2006/0106263 A1 | * | 5/2006 | Miller et al. | .................. 570/155 |
| 2007/0096053 A1 | * | 5/2007 | Nair et al. | ........................ 252/67 |

FOREIGN PATENT DOCUMENTS

| | | |
|---|---|---|
| JP | 8-193039 | 7/1996 |
| WO | 20080002501 | 1/2008 |
| WO | 20080030442 | 3/2008 |
| WO | 20080030444 | 3/2008 |
| WO | 20080054778 | 5/2008 |
| WO | 20080060612 | 5/2008 |
| WO | 20080060614 A2 | 5/2008 |
| WO | 20080075017 | 6/2008 |

OTHER PUBLICATIONS

Aoyama et al: "Preparation of Hexafluoropropene" Caplus, Jan. 1, 1996 XP002484314 Abstract.

* cited by examiner

*Primary Examiner* — Jafar Parsa

(57) ABSTRACT

A process is disclosed for making $CF_3CF=CHF$ or a mixture thereof with $CF_2=CFCHF_2$. The process involves (i) contacting $CH_2ClCF_2CF_3$, and optionally $CH_2FCF_2CClF_2$, in a reaction zone in the presence of a catalytically effective amount of dehydrofluorination catalyst to produce $CHCl=CFCF_3$, and, if $CH_2FCF_2CClF_2$ is present, $CHF=CFCClF_2$; (ii) contacting $CHCl=CFCF_3$ and $CHF=CFCClF_2$, if any, formed in (i) with hydrogen fluoride (HF) in a reaction zone, optionally in the presence of a fluorination catalyst, to produce a product mixture comprising $CHF=CFCF_3$, and, if $CHF=CFCClF_2$ is present, $CF_2=CFCHF_2$; and (iii) recovering $CF_3CF=CHF$, or a mixture thereof with $CF_2=CFCHF_2$, from the product mixture formed in (ii); and optionally (iv) separating at least a portion of any $CF_3CF=CHF$ in the product mixture formed in (ii) from the $CF_2=CFCHF_2$ in the product mixture formed in (ii). Also disclosed is an azeotropic composition involving $CHCl=CFCF_3$, $CHF=CFCClF_2$ and HF.

10 Claims, No Drawings

PROCESSES FOR PRODUCING PENTAFLUOROPROPENES AND CERTAIN AZEOTROPES COMPRISING HF AND CERTAIN HALOPROPENES OF THE FORMULA $C_3HClF_4$

FIELD OF THE INVENTION

The present invention relates to processes that involve the production of halogenated hydrocarbon products comprising 1,2,3,3,3-pentafluoropropene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a ($CF_3CH_2F$) being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is considerable interest in developing new refrigerants with reduced global warming potential, as well as zero ozone depletion potential, for the mobile air-conditioning market, and in other refrigeration applications.

HFC-1225ye ($CF_3CF=CHF$), having zero ozone depletion and a low global warming potential, has been identified as a potential refrigerant. U.S. Pat. No. 5,396,000 discloses a process for producing HFC-1225ye by dehydrofluorination of $CF_3CFHCF_2H$ (HFC-236ea). There is a need for new manufacturing processes for the production of HFC-1225ye.

1,1,2,3,3-Pentafluoro-1-propene ($CF_2=CFCHF_2$, HFC-1225yc) is useful as a monomer for the manufacture of fluoropolymers.

SUMMARY OF THE INVENTION

The present invention provides a process for making $CF_3CF=CHF$ (HFC-1225ye) or a mixture thereof with $CF_2=CFCHF_2$ (HFC-1225yc). The process comprises (i) contacting $CH_2ClCF_2CF_3$ (HCFC-235cb), and optionally $CH_2FCF_2CClF_2$ (HCFC-235cc), in a reaction zone in the presence of a catalytically effective amount of dehydrofluorination catalyst to produce E- and/or Z—$CHCl=CFCF_3$ (HCFC-1224yd), and, if $CH_2FCF_2CClF_2$ (HCFC-235cc) is present, E- and/or Z—$CHF=CFCClF_2$ (HCFC-1224ye); (ii) contacting E- and/or Z—$CHCl=CFCF_3$ (HCFC-1224yd) and, E- and/or Z—$CHF=CFCClF_2$ (HCFC-1224ye), if any, formed in (i) with hydrogen fluoride (HF) in a reaction zone, optionally in the presence of a fluorination catalyst, to produce a product mixture comprising E- and/or Z—$CHF=CFCF_3$ (HFC-1225ye), and, if E- and/or Z—$CHF=CFCClF_2$ (HCFC-1224ye) is present, $CF_2=CFCHF_2$ (HFC-1225yc); and (iii) recovering $CF_3CF=CHF$ (HFC-1225ye), or a mixture thereof with $CF_2=CFCHF_2$ (HFC-1225yc), from the product mixture formed in (ii); and optionally (iv) separating at least a portion of any E- and/or Z—$CF_3CF=CHF$ (HFC-1225ye) in the product mixture formed in (ii) from the $CF_2=CFCHF_2$ (HFC-1225yc) in the product mixture formed in (ii).

The present invention also provides a composition comprising (a) a mixture of E- and/or Z—$CHCl=CFCF_3$ (HCFC-1224yd) and E- and/or Z—$CHF=CFCClF_2$ (HCFC-1224ye) and (b) HF; wherein the HF is present in an effective amount to form an azeotropic combination with said mixture of E- and/or Z—$CHCl=CFCF_3$ (HCFC-1224yd) and E- and/or Z—$CHF=CFCClF_2$ (HCFC-1224ye).

DETAILED DESCRIPTION

The present invention provides a process for making HFC-1225ye or mixtures thereof with HFC-1225yc employing a multi-step process. As noted above the multi-step process involves HCFC-1224yd and in some embodiments, HCFC-1224ye, as intermediate reaction products. HFC-1225ye, HCFC-1224yd and HCFC-1224ye may exist as one of two configurational isomers, E- or Z—. HFC-1225ye as used herein refers to the isomers, E-HFC-1225ye (CAS Reg No. [5595-10-8]) or Z—HFC-1225ye (CAS Reg. No. [552843-8]), as well as any combinations or mixtures of such isomers. HCFC-1224yd as used herein refers to the isomers, E-HCFC-1224yd (CAS Reg. No. [111512-52-8]) or Z—HCFC-1224ye (CAS Reg. No. [111512-60-8]), as well as any combinations or mixtures of such isomers. HCFC-1224ye as used herein refers to the isomers, E-HCFC-1224ye (CAS Reg. No. [84195-40-4]) or Z—HCFC-1224ye, as well as any combinations or mixtures of such isomers.

In the first step of the process, HCFC-235cb, and optionally HCFC-235cc, is dehydrofluorinated over a suitable catalyst for a time sufficient to convert at least a portion of HCFC-235 (that is, the total of HCFC-235cb and HCFC-235cc) to HCFC-1224 (that is, the total of HCFC-1224yd and HCFC-1224ye). Dehydrofluorination of HCFC-235cb produces HCFC-1224yd. If HCFC-235cc is present during the contacting step, the HCFC-1224 produced comprises HCFC-1224ye. Of note are embodiments wherein the $C_3H_2ClF_5$ component (that is, the total of HCFC-235cb and HCFC-235cc) subjected to dehydrofluorination is primarily HCFC-235cb. Of particular note are embodiments wherein the $C_3H_2ClF_5$ subjected to dehydrofluorination is essentially free of HCFC-235cc.

Mixtures of HCFC-235cb and HCFC-235cc can be prepared by the reaction of chlorofluoromethane ($CH_2ClF$) with tetrafluoroethylene ($CF_2=CF_2$) in the presence of an aluminum halide as disclosed in U.S. Patent Application No. 60/855,513, filed Oct. 31, 2006, which is herein incorporated by reference in its entirety (see also PCT/US2007/022991, filed Oct. 31, 2007). In particular, $C_3H_2ClF_5$ (i.e., HCFC-235cb and HCFC-235cc) can be produced by reacting $CH_2ClF$ with $CF_2=CF_2$ in a reaction zone in the presence of a catalytically effective amount of composition having a bulk formula of $AlCl_xBr_yF_{3-x-y}$ wherein the average value of x is 0 to 3, the average value of y is 0 to 3−x, provided that the average values of x and y are not both 0.

HCFC-235cb, free of HCFC-235cc, can be prepared by the reaction of potassium chloride with p-$CH_3C_6H_4SO_2CH_2C_2F_5$ as reported by McBee, et al. in Journal of the American Chemical Society, Volume 77, pages 3149-3151 (1955) or by the chlorination of $CH_3CF_2CF_3$ as disclosed by Boudakian, et. al. in British Patent No. 1,171,202.

The dehydrofluorination reaction may be conducted in the vapor phase in a reaction zone containing the dehydrofluorination catalyst at temperatures of from about 200° C. to about 500° C. and preferably from about 300° C. to about 450° C.

The contact time is typically from about 1 to about 450 seconds, preferably from about 10 to about 120 seconds.

The reaction pressure can be sub-atmospheric, atmospheric or super-atmospheric. Near atmospheric pressures are preferred. However, the dehydrofluorination of $C_3HCl_2F_5$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $C_3H_2ClF_5$ is from about 5:1 to 1:1. Nitrogen is the preferred inert gas.

Typical dehydrofluorination reaction conditions and dehydrofluorination catalysts are disclosed in U.S. Pat. No. 5,396,000, which is incorporated herein by reference in its entirety. Preferably, the dehydrofluorination catalyst comprises at least one catalyst selected from the group consisting of carbon, aluminum fluoride, fluorided alumina, and trivalent chromium oxide.

Other dehydrofluorination catalysts useful for converting $C_3H_2ClF_5$ to HCFC-1224 are described in U.S. Pat. No. 6,093,859 and U.S. Pat. No. 6,369,284; the teachings of these disclosures are incorporated herein by reference The effluent from the dehydrofluorination reactor typically includes HF, HCFC-1224yd, $CF_3CHFCHClF$ (HCFC-235ea) and any unconverted HCFC-235cb. When HCFC-235cc is present as a starting material, the effluent typically also contains HCFC-1224ye, $CClF_2CHFCHF_2$ (HCFC-235eb) and any unconverted HCFC-235cc.

The HCFC-1224yd, and HCFC-1224ye if present, may be separated from the product mixture formed in the dehydrofluorination reactor by methods known to the art. Since HF is present in the effluent, if desired, this separation can also include isolation of an azeotrope or near azeotrope composition of HCFC-1224yd and HF. The azeotrope or near azeotrope composition of HCFC-1224yd and HF is disclosed in above-referenced U.S. Patent Application No. 60/855,513. If HCFC-1224ye is present in the reactor effluent, this separation, if desired, can also include isolation of an azeotrope or near azeotrope composition of a mixture of HCFC-1224yd and HCFC-1224ye and HF. The ratio of HCFC-1224yd to HCFC-1224ye, present in the HCFC-1224 mixture forming the azeotrope or near azeotrope with HF, can vary depending on the ratio of HCFC-235cb and HCFC-235cc fed and/or converted in the dehydrofluorination reactor. HF-free HCFC-1224yd, or HF-free HCFC-1224yd/HCFC-1224ye mixture, may be obtained using procedures similar to those disclosed in U.S. Patent Application Publication No. 2006/0106263, incorporated herein by reference. Unreacted HCFC-235cb (and HCFC-235cc if present in the starting material), can be recycled back to the dehydrofluorination reactor.

In the second step of the process of the invention, HCFC-1224 is fluorinated in a reaction zone, optionally in the presence of a fluorination catalyst, for a time sufficient to convert at least a portion of HCFC-1224 to HFC-1225 (that is, HFC-1225ye and HFC-1225yc). Fluorination of HCFC-1224yd produces HFC-1225ye. If HCFC-1224ye is present during the fluorination reaction, the fluorination product also comprises HFC-1225yc. Of note are embodiments wherein the $C_3HClF_4$ component (that is, the total of HCFC-1224yd and HCFC-1224ye) subjected to fluorination is primarily HCFC-1224yd. Of particular note are embodiments wherein the $C_3HClF_4$ component, subjected to fluorination is essentially free of HCFC-1224ye.

The fluorination is preferably conducted in the vapor phase in the presence of a fluorination catalyst. Suitable fluorination catalysts which may be used in the vapor phase reaction of the invention include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts, (optionally supported on alumina, aluminum fluoride, fluorided alumina, or carbon), include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to about 20 percent by weight based on the total weight of the catalyst; typically from about 0.1 to about 10 percent by weight based on the total weight of the catalyst.

Of note are vapor phase fluorination embodiments wherein the fluorination catalysts include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, $2^{nd}$ edition (McGraw-Hill, New York, 1991).

Optionally, the fluorination catalysts described above can be pretreated with HF. This pretreatment can be accomplished, for example, by placing the metal-containing catalyst in a suitable container, and thereafter, passing HF over the metal-containing catalyst. In one embodiment of this invention, such container can be the reactor used to perform the fluorination reaction in this invention. Typically, the pretreatment time is from about 15 to about 300 minutes, and the pretreatment temperature is from about 200° C. to about 450° C.

Suitable temperatures for the vapor-phase fluorination of HCFC-1224 are from about 120° C. to about 500° C., preferably from about 200° C. to about 450° C. and most preferably from about 250° C. to about 350° C. Suitable reactor pressures for the vapor-phase fluorination reactor may be from about 1 to about 30 atmospheres. A reactor pressure of from about 1 atmosphere to about 5 atmospheres is preferred. A suitable reaction time may vary from about 1 to about 120 seconds, preferably from about 5 to about 60 seconds.

The molar ratio of HF to the total amount of HCFC-1224 for the vapor phase fluorination reaction is typically from about the stoichiometric ratio of HF to the total amount of HCFC-1224 to about 30:1 and is preferably from about 2:1 to about 10:1.

Of note are embodiments wherein the HF present in the product mixture from the dehydrofluorination is not separated from the HCFC-1224 produced in (i), and the HCFC-1224 and HF from the dehydrofluorination is fed to fluorination reactor (e.g., as an azeotrope and/or as a non-azeotropic mixture).

The effluent from the reaction zone of the vapor-phase fluorination reactor typically includes HCl, HF, HFC-1225ye, $CF_3CHFCHF_2$ (HFC-236ea), and any unreacted HCFC-1224yd. If HCFC-1224ye is fed to the reactor, the effluent typically also includes HFC-1225yc, and any unreacted HCFC-1224ye. Any unreacted HCFC-1224 (that is HCFC-1224yd and HCFC-1224ye), alone, or combined as HF azeotrope or near azeotrope, is recycled back to the vapor-phase fluorination reactor.

The desired HFC-1225ye, and mixtures thereof with HFC-1225yc from the reactor effluent, is separated by methods known to the art. Optionally, a portion of HFC-1225ye can be separated from mixtures of HFC-1225ye and HFC-1225yc by known methods such as distillation.

Since HF is present in the effluent from the vapor-phase fluorination reactor, if desired, this separation can also include isolation of azeotrope or near azeotrope compositions of HFC-1225ye and HF, and, azeotrope or near azeotrope compositions of HFC-1225yc and HF (if HCFC-1224ye is present as part of the $C_3HClF_4$ component in the fluorination reactor), and further processing to produce HF-free HFC-1225ye and HF-free HFC-1225yc by using procedures similar to that disclosed in U.S. Patent Application Publication No. 2006/0106263, which is incorporated herein by reference. The azeotrope and near azeotrope of HFC-1225yc and HF is disclosed in U.S. Patent Application No. 60/859,186 filed Nov. 15, 2006.

It is noted that any HCFC-1224ye in the product of step (i) need not be forwarded to step (ii); and that any HFC-1225yc in the product of step (ii) need not be recovered. Accordingly, a process is provided for making $CF_3CF=CHF$, comprising (i) contacting $CH_2ClCF_2CF_3$, and optionally $CH_2FCF_2CClF_2$, in a reaction zone in the presence of a catalytically effective amount of dehydrofluorination catalyst to produce $CHCl=CFCF_3$, and, if $CH_2FCF_2CClF_2$ is present, $CHF=CFCClF_2$; (ii) contacting $CHCl=CFCF_3$, and optionally $CHF=CFCClF_2$, if any, formed in (i) with hydrogen fluoride (HF) in a reaction zone, optionally in the presence of a fluorination catalyst, to produce a product mixture comprising $CHF=CFCF_3$; and (iii) recovering $CF_3CF=CHF$, from the product mixture formed in (ii).

HFC-1225ye can be used for the production of HFC-1234yf. Of note is a process for production of HFC-1234yf using HFC-1225ye characterized by said HFC-1225ye being produced by the method disclosed herein. HFC-1234yf may be produced from the HFC-1225ye by adding hydrogen and $CF_3CF=CHF$ to a reaction vessel containing a hydrogenation catalyst; reacting said $CF_3CF=CHF$ with hydrogen over said hydrogenation catalyst to produce $CF_3CHFCH_2F$; and dehydrofluorinating $CF_3CHFCH_2F$ in the vapor phase over a dehydrofluorination catalyst. Suitable dehydrofluorination catalysts are selected from the group consisting of aluminum fluoride; gamma alumina, fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, cobalt-substituted chromium oxides, and cubic chromium trifluoride; carbon, acid-washed carbon, activated carbon, three dimensional matrix carbonaceous materials; and metal compounds supported on carbon, to produce $CF_3CF=CH_2$. Further details regarding the production of HFC-1234yf from HFC-1225ye are provided in International Application No. PCT/US2007/19315, which is hereby incorporated herein by reference.

The consideration of processes for the separation of individual products by distillation from the various product mixtures obtained from the different reaction steps of the processes of this invention includes the azeotropic combinations of the individual products thereof with HF.

As recognized in the art, an azeotropic composition is a constant boiling or substantially constant boiling liquid admixture of two or more different substances, wherein the admixture distills without substantial composition change and behaves as a constant boiling composition. Accordingly, the essential features of an azeotropic composition are that at a given pressure, the boiling point of the liquid composition is fixed and that the composition of the vapor above the boiling composition is essentially that of the boiling liquid composition (i.e., no substantial fractionation of the components of the liquid composition takes place). It is also recognized in the art that both the boiling point and the weight percentages of each component of the azeotropic composition may change when the azeotrope composition is subjected to boiling at different pressures. Thus, an azeotropic composition may be defined in terms of the unique relationship that exists among the components or in terms of the compositional ranges of the components or in terms of the weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432-439). Experimental identification of azeotropic compositions involving the same components may be used to confirm the accuracy of such calculations and/or to modify the calculations at the same temperature and pressure or at other temperatures and pressures.

As noted above, the present invention provides azeotropic compositions comprising hydrogen fluoride combined with a mixture of HCFC-1224yd and HCFC-1224ye. In accordance with this invention, compositions are provided which comprise HCFC-1224yd, HCFC-1224ye and HF, wherein the HF is present in an effective amount to form an azeotropic combination with the HCFC-1224yd and HCFC-1224ye. According to calculations, these compositions include embodiments comprising from about 80 mole percent to about 50 mole percent HF and from about 20 mole percent to about 50 mole percent total HCFC-1224yd and HCFC-1224ye (which form azeotropes boiling at temperatures between about −25° C. and about 100° C. and at pressures between about 3 psia (20.7 kPa) and about 300 psia (2070 kPa)). Compositions may be formed that consist essentially of azeotropic combinations of hydrogen fluoride with HCFC-1224yd and HCFC-1224ye. These include compositions calculated to consist essentially of from about 80 mole percent to about 50 mole percent HF and from about 20 mole percent to about 50 mole percent total HCFC-1224yd and HCFC-1224ye (which form azeotropes boiling at temperatures between about −25° C. and about 100° C. and at pressures between about 3 psia (20.7 kPa) and about 300 psia (2070 kPa)). Azeotropic compositions of HF, HCFC-1224yd and HCFC-1224ye are useful as sources of HF in fluorination reactions. For example by combining the azeotrope of HF, HCFC-1224yd and HCFC-1224ye with fluorination precursor compounds it is possible to obtain HF-free HCFC-1224yd and HCFC-1224ye and a fluorinated product (see for example, U.S. Pat. No. 6,224,781).

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The processes of the present invention are demonstrated by the following prophetic examples.

Example 1

Dehydrofluorination of HCFC-235cb ($CF_3CF_2CH_2Cl$)

An Inconel™ tube (⅝ inch OD (1.59 cm)) is charged with chromium oxide pellets (5 cc, 7.18 g, 12-20 mesh (1.68-0.84 mm)). The tube is connected to a reactor system and surrounded with an electrically-heated furnace. The chromium oxide is prepared by the pyrolysis of ammonium dichromate as described in U.S. Pat. No. 5,036,036, herein incorporated by reference. The catalyst is then activated according to the following sequence (time in hours, flow rate nitrogen, flow rate HF, temperature):

1 h, $8.3 \times 10^{-8}$ m$^3$/s, 0, 200° C.; 1 h, $8.3 \times 10^{-8}$ m$^3$/s, 0, 400° C.; 1 h, $8.3 \times 10^{-8}$ m$^3$/s, 0, 300° C.; 1 h, $5.8 \times 10^{-7}$ m$^3$/s, $2.0 \times 10^{-7}$ m$^3$/s, 300° C.; 1 h, $5.8 \times 10^{-7}$ m$^3$/s, $2.0 \times 10^{-7}$ m$^3$/s, 350° C.; 1 h, $5.8 \times 10^{-7}$ m$^3$/s, $2.0 \times 10^{-7}$ m$^3$/s, 375° C.; 0.5 h, $5.8 \times 10^{-7}$ m$^3$/s, $2.0 \times 10^{-7}$ m$^3$/s, 400° C.; 0.5 h, $5.8 \times 10^{-7}$ m$^3$/s, $2.0 \times 10^{-7}$ m$^3$/s, 425° C.; 0.5 h, $4.2 \times 10^{-7}$ m$^3$/s, $3.3 \times 10^{-7}$ m$^3$/s, 425° C.; 0.5 h, $2.5 \times 10^{-7}$ m$^3$/s, $4.7 \times 10^{-7}$ m$^3$/s, 425° C.; and 0.5 h, $5.0 \times 10^{-8}$ m$^3$/s, $6.0 \times 10^{-7}$ m$^3$/s, 425° C. The flow of hydrogen fluoride is then stopped and the reactor is purged with nitrogen.

A mixture of HCFC-235cb and nitrogen in a molar ratio of 1:3 is then passed through the catalyst bed with a contact time of about 30 seconds at a temperature of 350° C. The pressure in the reactor is nominally atmospheric. Analysis of the reactor effluent shows at least 50% of the HCFC-235cb is converted and the major reaction product is HCFC-1224yd (E/Z—CF$_3$CF═CHCl).

Example 2

Fluorination of HCFC-1224yd (CF$_3$CF═CHCl)

A metal oxide fluorination catalyst comprising 95 atom % chromium and 5 atom % zinc is prepared by co-precipitation of a mixture of chromium and zinc hydroxides as disclosed in U.S. Pat. No. 7,285,691. The mixture is dried and calcined at 900° C.

The calcined catalyst is pelletized (12-20 mesh (1.68-0.84 mm)) and 14 g (10 cc) of the solid is placed in a 30.5 cm×1.27 cm o.d. Hastelloy® tube. The tube is connected to a reactor system and is surrounded with an electrically-heated furnace. The tube is heated from 50° C. to 175° C. in a flow of nitrogen (50 cc/min; $8.3(10)^{-7}$ m$^3$/sec) over the course of about one hour. HF is then admitted to the reactor at a flow rate of 50 cc/min ($8.3(10)^{-7}$ m$^3$/sec). After 2 hours, the nitrogen flow is decreased to 20 cc/min ($3.3(10)^{-7}$ m$^3$/sec) and the HF flow is increased to 80 cc/min ($1.3(10)^{-6}$ m$^3$/sec); this flow is maintained for about 1 hour. The reactor temperature is then gradually increased to 400° C. over 5 hours. At the end of this period, the HF flow is stopped and the reactor cooled to 300° C. under 20 sccm ($3.3(10)^{-7}$ m$^3$/sec) nitrogen flow.

A mixture of hydrogen fluoride and an E/Z-mixture of HCFC-1224yd is then fed to the catalyst at 300° C. with a contact time of 30 seconds; the molar ratio of HF to HCFC-1224yd is 8:1. The pressure in the reactor is nominally atmospheric. Under these conditions, at least 50% of the HCFC-1224yd is converted with E/Z—CF$_3$CF═CHF being the major reaction product. The effluent also contains unreacted starting materials and lesser amounts of CF$_3$CHFCHF$_2$.

What is claimed is:

1. A process for making CF$_3$CF═CHF, comprising:
   (i) contacting CH$_2$ClCF$_2$CF$_3$ in a reaction zone in the presence of a catalytically effective amount of dehydrofluorination catalyst to produce CHCl═CFCF$_3$;
   (ii) contacting CHCl═CFCF$_3$ formed in (i) with hydrogen fluoride (HF) in a reaction zone, optionally in the presence of a fluorination catalyst, to produce a product mixture comprising CHF═CFCF$_3$; and
   (iii) recovering CF$_3$CF═CHF, from the product mixture formed in (ii).

2. The process of claim 1 wherein the C$_3$H$_2$ClF$_5$ dehydrofluorinated in (i) is prepared by reacting CH$_2$ClF with CF$_2$═CF$_2$ in a reaction zone in the presence of a catalytically effective amount of an aluminum halide composition having a bulk formula of AlCl$_x$Br$_y$F$_{3-x-y}$ wherein the average value of x is 0 to 3, the average value of y is 0 to 3−x, provided that the average values of x and y are not both 0.

3. The process of claim 1 wherein the C$_3$H$_2$ClF$_5$ dehydrofluorinated in (i) is essentially free of CH$_2$FCF$_2$CClF$_2$.

4. The process of claim 1 wherein the C$_3$HClF$_4$ fluorinated in (ii) is essentially free of CHF═CFCClF2.

5. A process for producing HFC-1234yf using HFC-1225ye, characterized by making said HFC-1225ye by the process of claim 1.

6. The process of claim 5 comprising the steps of:
   (A) adding hydrogen and CF$_3$CF═CHF to a reaction vessel containing a hydrogenation catalyst;
   (B) reacting said CF$_3$CF═CHF with hydrogen over said hydrogenation catalyst to produce CF$_3$CHFCH$_2$F; and
   (C) dehydrofluorinating CF$_3$CHFCH$_2$F in the vapor phase over a dehydrofluorination catalyst.

7. A composition comprising (a) a mixture of CHCl═CFCF$_3$ and CHF═CFCClF$_2$ and (b) HF; wherein the HF is present in an effective amount to form an azeotropic combination with said mixture of CHCl═CFCF$_3$ and CHF═CFCClF$_2$.

8. A process as in claim 1, comprising: (i) contacting CH$_2$ClCF$_2$CF$_3$, further comprising CH$_2$FCF$_2$CClF$_2$, in a reaction zone in the presence of a catalytically effective amount of dehydrofluorination catalyst to produce CHCl═CFCF$_3$, and CHF═CFCClF$_2$;
   (ii) contacting said CHCl═CFCF$_3$ and CHF═CFCClF$_2$ formed in (i) with hydrogen fluoride (HF) in a reaction zone, optionally in the presence of a fluorination catalyst, to produce a product mixture comprising CHF═CFCF$_3$; and
   (iii) recovering CF$_3$CF═CHF, from the product mixture formed in (ii).

9. The azeotropic composition of claim 7, wherein said composition comprises from about 20 mole percent to about 50 mole percent of said mixture of CHCl═CFCF$_3$ and CHF═CFCClF$_2$ and from about 50 mole percent to about 80 mole percent of HF, having a vapor pressure of from about 3 psia to about 300 psia, at a temperature of from about −25° C. to about 100° C.

10. The composition of claim 7, wherein said composition consists essentially of from about 20 mole percent to about 50 mole percent of said mixture of CHCl═CFCF$_3$ and CHF═CFCClF$_2$ and from about 50 mole percent to about 80 mole percent of HF, having a vapor pressure of from about 3 psia to about 300 psia, at a temperature of from about −25° C. to about 100° C.

* * * * *